United States Patent [19]
Kaster et al.

[11] Patent Number: 5,403,333
[45] Date of Patent: Apr. 4, 1995

[54] SIDE-TO-END VASCULAR ANASTOMOTIC STAPLE APPARATUS

[75] Inventors: Robert L. Kaster, Plymouth; Perry M. Domaas, Brooklyn Center, both of Minn.

[73] Assignee: Robert L. Kaster, Plymouth, Minn.

[21] Appl. No.: 103,196

[22] Filed: Aug. 6, 1993

Related U.S. Application Data

[62] Division of Ser. No. 573,856, Aug. 28, 1990, Pat. No. 5,234,447.

[51] Int. Cl.$^6$ .............................................. A61B 17/00
[52] U.S. Cl. .................................. 606/151; 606/153; 606/219; 227/175; 227/179
[58] Field of Search .............................. 606/151–153, 606/155, 139, 213, 219; 227/175, 178, 179, 181, 19

[56] References Cited

U.S. PATENT DOCUMENTS

| | | | |
|---|---|---|---|
| 1,150,358 | 8/1915 | Gilmer . | |
| 1,151,300 | 8/1915 | Soresi . | |
| 2,558,132 | 6/1951 | Green . | |
| 3,221,746 | 12/1965 | Noble . | |
| 3,416,821 | 12/1968 | Benno . | |
| 3,519,187 | 7/1970 | Kapitanov et al. | 606/153 |
| 3,774,615 | 11/1973 | Lim et al. . | |
| 3,908,662 | 9/1975 | Razgulov et al. | 606/155 |
| 4,157,676 | 6/1979 | Jureit . | |
| 4,352,358 | 10/1982 | Angelchik . | |
| 4,368,736 | 1/1983 | Kaster | 606/153 |
| 4,505,414 | 3/1985 | Filipi | 227/19 |
| 4,523,592 | 6/1985 | Daniel . | |
| 4,957,499 | 9/1990 | Lipatov | 606/153 |
| 5,015,249 | 5/1991 | Nakao et al. | 606/142 |
| 5,100,418 | 3/1992 | Yoon et al. | 606/151 |
| 5,104,399 | 4/1992 | Lazarus | 606/153 |
| 5,217,030 | 6/1993 | Yoon | 606/151 |

FOREIGN PATENT DOCUMENTS

| | | | |
|---|---|---|---|
| 0121533 | 1/1960 | U.S.S.R. | 606/221 |

Primary Examiner—Stephen C. Pellegrino
Assistant Examiner—Jeffrey A. Schmidt
Attorney, Agent, or Firm—Kinney & Lange

[57] ABSTRACT

A side-to-end vascular anastomosis stapling apparatus that includes a stapling tool (10), a staple forming tool (11) and a staple (12). The stapling tool (10) includes a sleeve (13), a core unit (14), a mandrel (16) and a trigger unit (17). The core unit (14) includes a plurality of fingers (26) that can be selectively urged outwardly by interaction with the mandrel (16) to grip the staple (12). The staple (12) has a plurality of vessel and interior wall engaging members (43) and a plurality of exterior wall engaging members (44).

16 Claims, 3 Drawing Sheets

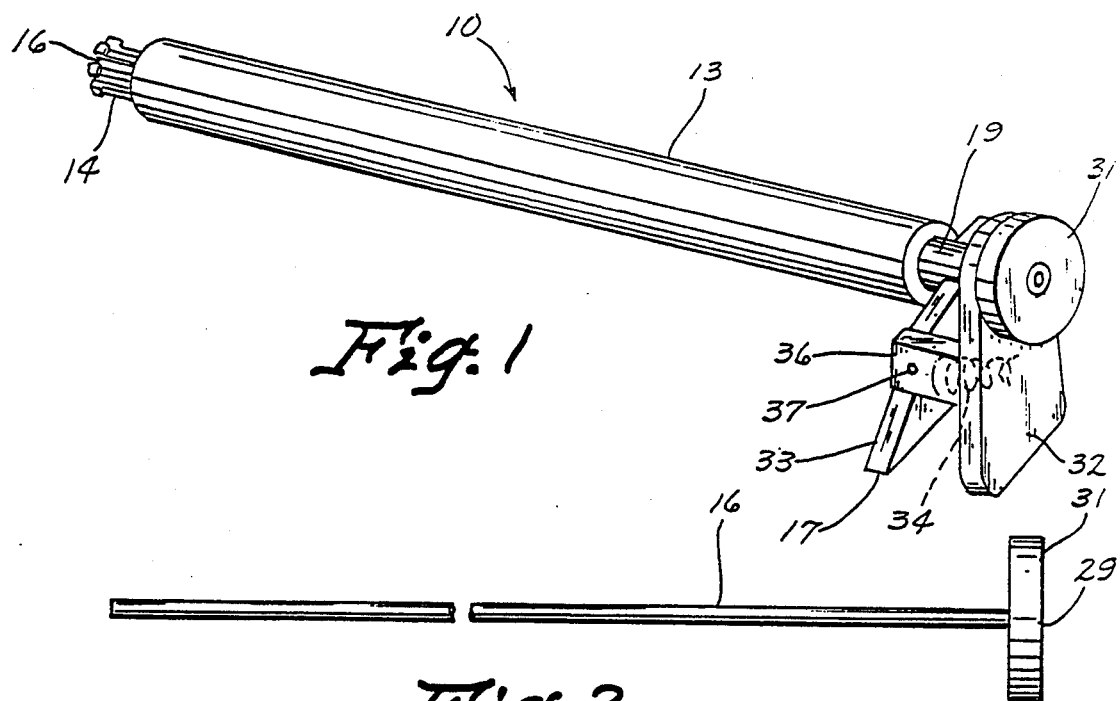
Fig. 1
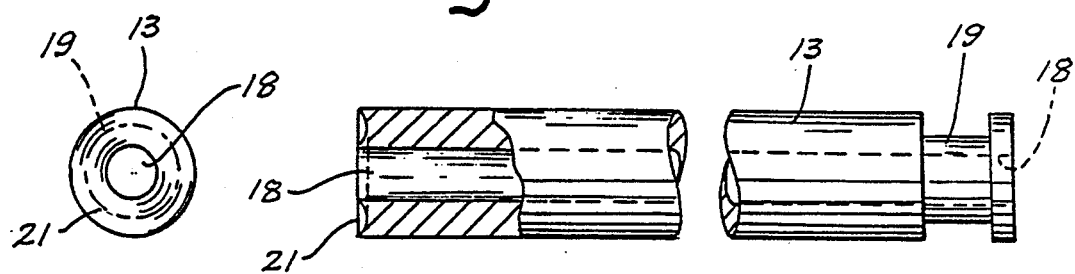
Fig. 2
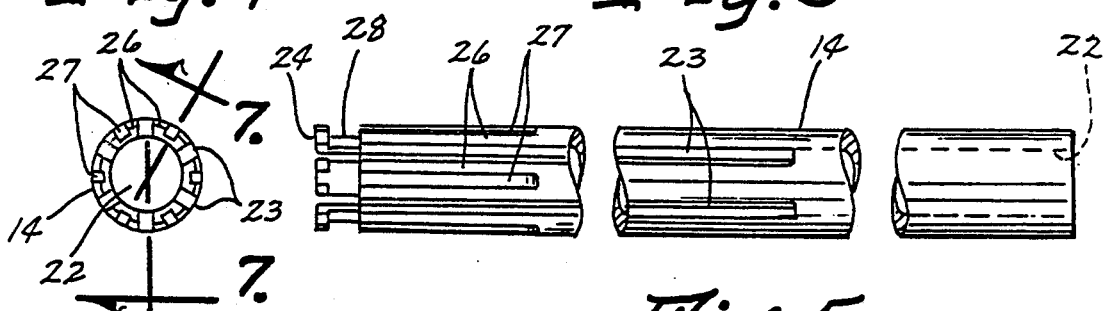
Fig. 4    Fig. 3
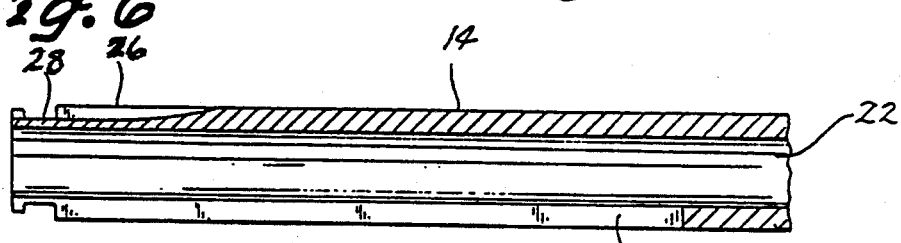
Fig. 6    Fig. 5
Fig. 7

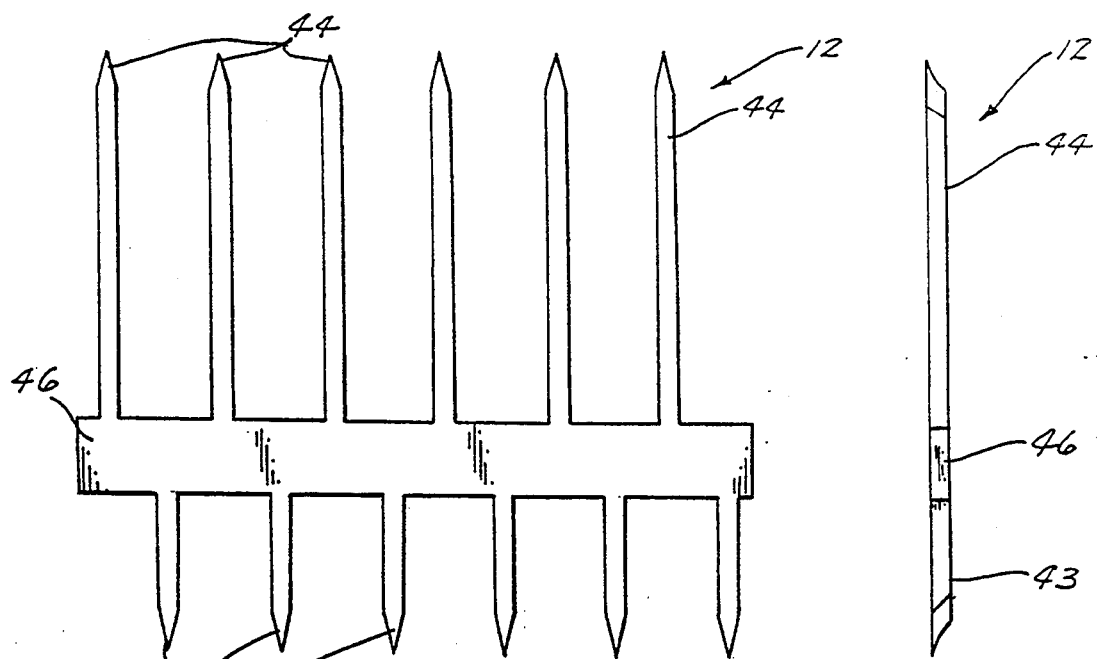
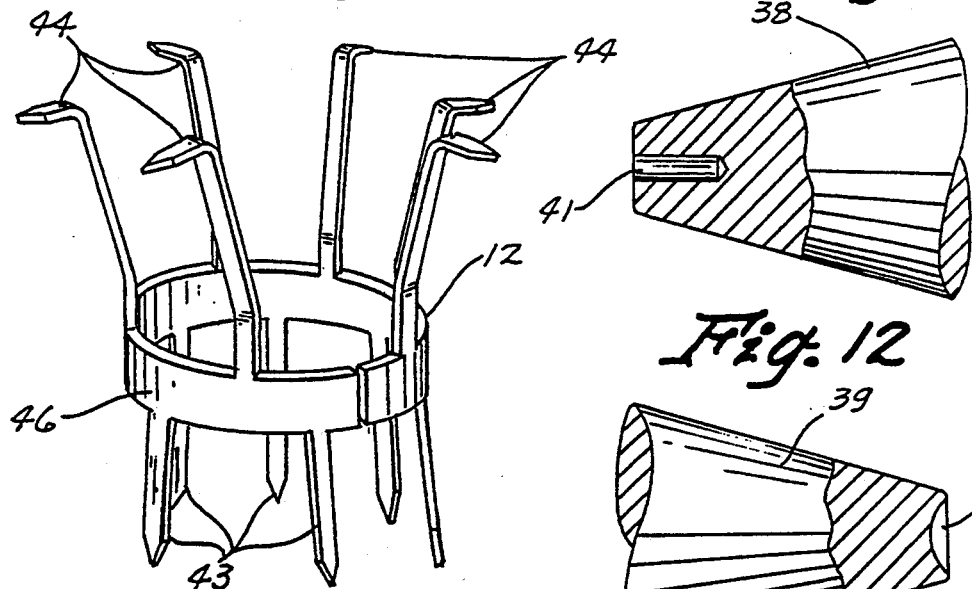
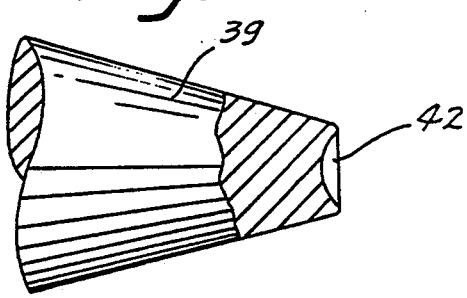
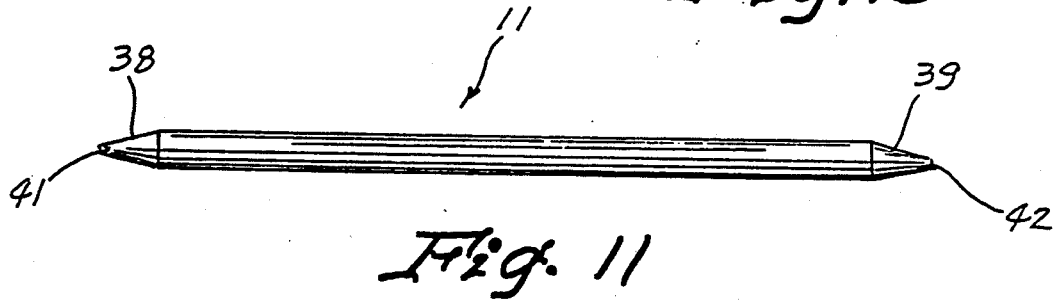

SIDE-TO-END VASCULAR ANASTOMOTIC STAPLE APPARATUS

This is a division of application Ser. No. 07/573,856, filed Aug. 28, 1990, now U.S. Pat. No. 5,234,447.

TECHNICAL FIELD

This invention relates generally to anastomotic connections of the ends of blood vessels to the sides of other blood vessels or other blood holding or transporting structures, such as the heart. The invention relates more particularly to the use of staples to realize such as anastomosis.

BACKGROUND ART

Anastomosis constitutes the joinder of parts or branches to allow intercommunication between them. In a surgical context, anastomosis occurs when a blood vessel becomes joined to another blood vessel or other blood filled object such that blood can flow freely through the established junction. Typically, side-to-end vascular anastomosis will be accomplished through use of sutures or specialized anastomotic connectors. These two options are often either time consuming or costly, and specialized connectors tend to expose non-organic material in the area of blood flow.

Although simple mechanical fastening devices such as staples have been known for more than two centuries, and staples have been used in surgery since the 1920's, such use has been largely restricted to surgery of the gastrointestinal tract. Few attempts have been made to provide for anastomotic stapling of vascular members. The efforts that have been made to provide for a stapled vascular anastomosis appear to deal with end-to-end vascular anastomosis, and not side-to-end.

The widespread use of staples for gastrointestinal tract surgery, as versus the limited or nonexistent use of staples for vascular surgery, can be easily explained. Blood vessels are typically comprised of remarkable thin tissues, whereas gastrointestinal tract tissues are generally fairly thick. Staples can be utilized with thicker materials in a relatively uncomplicated fashion. The use of staples for blood vessels, however, carries with it a high expected risk of rupture, tearing, or blood flow obstruction. As a result, even though stapling tools were provided in the early 1960's that would allow for end-to-end vascular anastomosis, this procedure is virtually unheard of in western medicine as of today. Side-to-end vascular anastomosis remains completely uncharted territory.

There exists a need for a side,to-end vascular anastomotic stapling apparatus that can be easily operated, will effectuate an anastomotic connection in a time and cost effective manner. The resulting stapled junction should minimize exposure of non-organic material in the are of blood flow, and the anastomosis itself should be reliable and substantially free of risk of infection or other similar problems.

DISCLOSURE OF THE INVENTION

These needs and, others are substantially met through provision of the side-to-end vascular anastomotic stapling apparatus disclosed in this specification. The apparatus is comprised very generally of a stapling tool, a staple forming tool and staple the apparatus has been particularly designed for use in side-to-end anastomosis, as where the end of a blood vessel becomes connected to the side or wall of a second blood vessel or other structure, such as the heart.

The stapling tool may be comprised in general of a sleeve, a core unit, a mandrel and a trigger unit.

The core unit may be formed of a plastic tube having a hole axially disposed through its entire length. The rearward end of the sleeve has a cavity formed peripherally thereabout for use in interfacing with the trigger unit. The forward end has an annularly shaped concave cavity formed therein to serve as an anvil.

The core unit may be comprised of a stainless steel tube that also has a hole axially disposed through its entire length. A plurality of slots are formed through its surface and parallel to its axis for a substantial portion of its length, thereby forming a plurality of fingers. Each finger has a groove formed therein and disposed substantially parallel to the slots and the axis of the core unit. So configured, the fingers are flexible in a radial direction. Finally, the core unit has a slot formed peripherally about its forward end to serve as a staple holding unit.

The exterior diameter of the core unit should be approximately the same as the interior diameter of the hole disposed axially through the sleeve, such that the core unit slidably disposed within the sleeve.

The mandrel may be comprised of a metal tube having a hole axially disposed through its entire length. The exterior diameter of the mandrel should be such that it may be slidably passed through the hole disposed axially through the core unit. To facilitate such sliding, a plastic tab may be affixed to one end of the mandrel to serve as a mandrel control unit.

The trigger unit includes a handle, a trigger and a bias unit. The handle affixes to the rearward end of the core unit. The trigger may be comprised of a movable plate that pivotally connects with respect to the sleeve and that interacts with the sleeve to cause the sleeve to move forward when the trigger is urged towards the handle. The bias unit includes a spring disposed between the handle and the trigger to urge the handle and trigger apart from one another.

The staple forming tool may be comprised of a plastic rod having two tapered ends. The first tapered end has a small hole formed therein. The second end has a small concave cavity formed therein.

The staples are each comprised of 316 surgical steel having a thickness of approximately 0.25 mm. (0.010 inches). Each staple has a plurality of vessel and interior wall engaging members, and a plurality of exterior wall engaging members. In addition, in the embodiment disclosed in this specification, a connecting unit serves to operably join both groups of members.

In use, a staple may be mounted on the stapling tool by positioning he connecting unit of the staple in the staple holding unit on the core unit. The staple should be positioned with the plurality of vessel and interior wall engaging members oriented forwardly and with the plurality of exterior wall engaging members oriented rearward. With the mandrel introduced fully through the core unit, the forward end of the mandrel will extend slightly beyond the core unit and coincidentally cause the fingers of the core unit to be outwardly disposed such that the staple will be held firmly in place.

A blood vessel (either biologic or artificial, in humans or in animals) may be disposed through the hole provided in the mandrel. With the blood vessel extending somewhat beyond the forward end of the mandrel, the blood vessel tissue may be everted back over the staple such that the plurality of vessel and interior wall engaging members pierce the blood vessel and extend therethrough. The staple forming tool may then be utilized to bend the vessel and interior wall engaging members back upon themselves.

Following this, the apparatus may be positioned to dispose the staple and blood vessel combination at the already provided hole in the wall of the blood vessel or other structure to which the blood vessel is to be connected. The tip of the apparatus, including the staple, may be pushed through this hole, and then pulled backwards to cause the vessel and interior wall engaging member's that are already piercing the blood vessel to also pierce and engage the interior wall of the second blood vessel or other structure.

While in this position, the trigger unit may be manipulated to cause the sleeve to move forward. This will cause the anvil positioned at the forward end of the sleeve to contact the exterior wall engaging members and urge them into a position to pierce and engage the exterior wall of the second blood vessel or other structure.

Following this, the mandrel may be removed by gripping the mandrel control unit and sliding it backwards through the core unit. Removal of the mandrel allows the fingers of the core unit to retract slightly, thus releasing their grip on the staple. The entire stapling tool may then be retracted from the area of the stapled anastomosis, and the anastomosis will be completed.

BRIEF DESCRIPTION OF THE DRAWINGS

These and other attributes of the invention will become more clear upon a thorough review and study of the following description of the best mode for carrying out the invention, particularly when reviewed in conjunction with the drawings, wherein:

FIG. 1 comprises a perspective view of the stapling tool;

FIG. 2 comprises a side elevational view of the mandrel;

FIG. 3 comprises a side elevational view of the sleeve;

FIG. 4 comprises a front elevational view of the sleeve;

FIG. 5 comprises a side elevational view of the core unit;

FIG. 6 comprises a front elevational view of the core unit;

FIG. 7 comprises a side elevational, sectioned, detailed view of the core unit;

FIG. 8 comprises an enlarged front elevational view of a staple;

FIG. 9 comprises an enlarged side elevational view of a staple;

FIG. 10 comprises an enlarged front elevational view of a formed staple;

FIG. 11 comprises a side elevational view of the staple forming tool;

FIG. 12 comprises an enlarged detailed view of one end of the staple forming tool;

FIG. 13 comprises an enlarged detailed view of the staple forming tool;

BEST MODE FOR CARRYING OUT THE INVENTION

Figure 14:
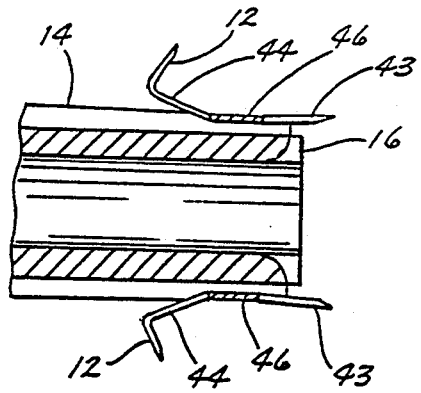
FIG. 14 comprises an enlarged side elevational detail view of the staple on the stapling tool.

Referring now to the drawings, the apparatus of the invention can be seen to be generally comprised of a stapling tool (10) (FIG. 1), a staple forming tool (11) (FIG. 11), and a staple (12) (FIG. 10). Referring to FIG. 1, the stapling tool (10) includes generally a sleeve (13), a core unit (14), a mandrel (16) (FIG. 2), and a trigger unit (17). Each of these generally described components of the stapling tool (10) will now be described in more detail in seriatim fashion.

Referring to FIGS. 3 and 4, the sleeve (13) may be comprised of a plastic tube having a hole (18) axially disposed therethrough. The rearward end of the sleeve (13) has a cavity (19) formed about the periphery thereof for interaction with the trigger unit as disclosed below. The forward end of the sleeve (13) has a concave shaped cavity (21) formed annularly about the hole (18). This cavity (21) serves as an anvil for the staple (12) described below.

In the embodiment depicted, the sleeve (13) has an overall length of approximately 141.91 mm. (5.587 inches) and a diameter of approximately 9.53 mm. (0.375 inches). The hole (18) has a diameter of approximately 3.96 mm. (0.156 inches).

Referring now to FIGS. 5, 6 and 7, the core unit (14) may be formed of a stainless steel tube having a hole (22) formed axially therethrough. A plurality of slots (23) are formed through the surface of the forward end of core unit (14) and are disposed substantially parallel to the axis of the core unit (14). These slots extend for an approximate length of 25 mm. from the forward end (24) of the core unit (14). By provision of these slots (23) a plurality of fingers (26) are formed. In the embodiment depicted, six slots (23) are provided to yield sir fingers (26). Each finger (26) has a groove (27)i formed therein and disposed substantially parallel to the slots (23) and the axis of the core unit (14). So configured, the fingers (26) are flexible in a radial direction.

Finally, it may be noted that a slot (28) has been formed about the periphery of the core unit (14) proximal the forward end (24) thereof. This slot (28) serves as a staple holding unit as disclosed in more detail below.

The core unit (14) has an overall length of approximately 152.40 mm. (6.0 inches) and a diameter of approximately 3.96 mm. (0.156 inches). So dimensioned, the core unit (14) can be slidably disposed within the hole (18) provided through the sleeve (13). The hole disposed through the core unit (14) has a diameter of approximately 2.54 mm. (0.10 inches)

Referring now to FIG. 2, the mandrel (16) may be comprised of a stainless steel tube having a hole (29) disposed axially therethrough. A mandrel control unit (31) comprising a plastic handle may be affixed to the rearward end thereof to allow the mandrel to be more easily grasped.

The mandrel tube has an overall length of approximately 157.15 mm. (6.187) inches and a diameter of approximately 2.54 mm. (0.10 inches). So configured, the mandrel (16) can be slidably inserted through the hole (22) provided through the core unit (14). In addition, when fully inserted into the core unit (14), the mandrel (16) will extend slightly beyond the forward end (24) of the core unit (14). The inner hole (29) of the mandrel (16) may be of an appropriate dimension to accommodate the desired sized blood vessels that will be used with the stapling tool (10).

Referring again to FIG. 1, the trigger unit (17) includes generally a handle (32), a trigger (33) and a bias unit (34). The handle(32) may be comprised of a plastic tab that may be connected to the rearward end of the core unit (14). Two flanges (36) are attached to either side of the handle (32) and extend forwardly. A pivot rod (37) connected between each flange (36) and the trigger (33). The trigger (33) may be comprised of another plastic tab having a notch formed in it for allowing it to be positioned about the sleeve (13) and having holes disposed therethrough to accommodate the pivot rod (37). The bias unit (34) may be comprised of a normally expanded spring that fits between the trigger (33) and the handle (32).

So configured, it will be appreciated that the biasing unit (34) will normally urge the trigger (17) away from the handle (32). The trigger (33) may, however, be selectively urged rearwardly towards the handle (32). When this happens, the trigger (33) will pivot about pivot rod (37), and this will cause the upward edges of the trigger (33) to contact the notched portion of the sleeve (13). This in turn will cause the sleeve (13) to move forwardly with respect to the core unit (14). The significance of this motion will be made more clear below.

Referring now to FIGS. 11,12 and 13, the staple forming tool (11) will be described. The staple forming tool may be comprised of a plastic rod having two cone shaped ends (38) and (39). Referring to FIG. 12, the first cone shaped end (38) has a narrow tube shaped hole (41) formed therein. Referring to FIG. 13, the second cone shaped end (39) has a concave cavity (42) formed therein.

The staple forming tool (11) has an overall length of approximately 127.0 mm. (5.0 inches). The hole (41) formed in the first end (38) of the staple forming tool (11) has a depth of approximately 1.27 mm. (050 inches) and a diameter of approximately 0.396 mm. (0.0156). The use of the staple forming tool (11) will be made more clear below.

Referring now to FIGS. 8 and 9, the staple (12) may be formed of 316 stainless steel having a thickness of approximately 0.25 mm. (0.010 inches). The staple includes a plurality of vessel and interior wall engaging members (43) and a plurality of exterior wall engaging members (44). Each of these members (43) and (44) are operably joined in this embodiment through use of a connecting unit (46) comprising a band. It will be appreciated that the vessel and interior wall engaging members (43) and the exterior wall engaging members (44) are all pointed and otherwise contoured to assure proper stapling action. The staple (12) may be formed through standard photo etching procession.

In this particular embodiment, the staple has an overall length of approximately 9.891 mm. (0.3894 inches). The vessel and interior wall engaging members (43) are approximately 2.34 mm. (0.92 inches) in length, and the exterior wall engaging members (44) are approximately 5.28 mm. (0.208 inches) in length.

Once formed in the manner described above, the staple (12) may be curved about a mandrel or other appropriate object to cause the connecting unit (46) to assume an annular shape as depicted in FIG. 10. Prior to the anastomotic procedure, the exterior wall engaging members (44) should each be bent twice through use of the staple forming tool (11) in the manner indicated, with the distal end curved at approximately 90° and the end more proximal to the connecting unit (46) bent slightly outward.

The method of using the apparatus may now be described.

A staple (12) (FIG. 14) may be positioned on the forward end (24) of the core unit (14) such that the connecting unit (46) of the staple (12) becomes lodged in the staple holding unit (28) of the core unit (14) with the vessel and interior wall engaging members (43) disposed forwardly and the exterior wall engaging members (44) disposed rearwardly. The mandrel (16) may then be fully disposed through the core unit (14). This positioning of the mandrel (16) will urge the fingers (26) of the core unit (14) slightly outward, and this will cause the staple (12) to be firmly held in place.

The end of the blood vessel to be connected to the wall of a second blood vessel or other structure may then be connected to a suture (not shown) in a manner well known to those skilled in the art of surgery. The suture may be easily inserted through the hole (29) in the mandrel (16) to cause the blood vessel to become similarly disposed therethrough. The blood vessel should be drawn through to extend approximately 3 mm. to 4 mm. beyond the forward end of the mandrel (16). The sutured end of the blood vessel may then be trimmed to remove the suture.

Figure 15:
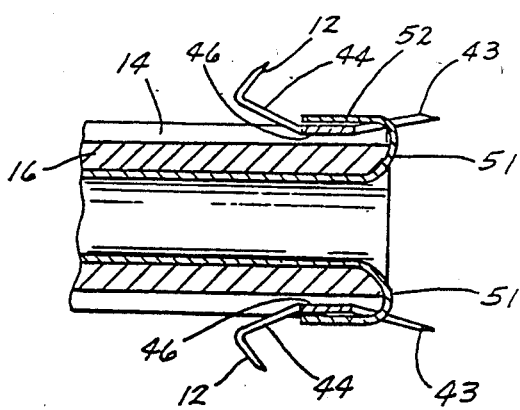
FIG. 15 comprises an enlarged side elevational detail view of the staple on the stapling tool with a blood vessel everted over it.

With reference to FIG. 15, the exposed end of the blood vessel (51) may then be everted back over the vessel and interior wall engaging members (43) such that the vessel and interior wall engaging members (43) pierce the blood vessel (51). The rearward end of the blood vessel may then be gently pulled in a rearward direction to firmly anchor the blood vessel (51) over the vessel and interior wall engaging members (43).

Figure 16:
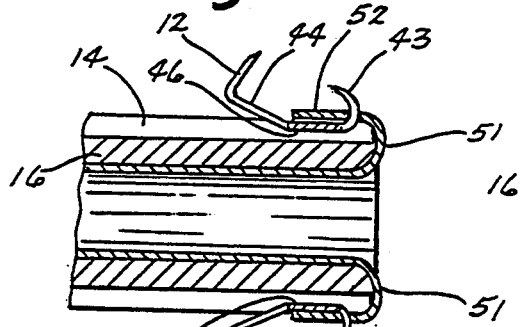
FIG. 16 comprises an enlarged side elevational detail view of the staple on the stapling tool with the vessel and interior wall engaging members bent rearwardly.

Following this, the hole (41) provided in the first end (38) of the staple forming tool (11) may be operably joined with each vessel and interior wall engaging member (43) such that an operator may cause the vessel and interior wall engaging members (43) to be bent radially approximately 90°. The second end (39) of the staple forming tool (11) may then be utilized to further urge the vessel and interior wall engaging members (43) substantially back upon themselves as depicted in FIG. 16.

Figure 17:
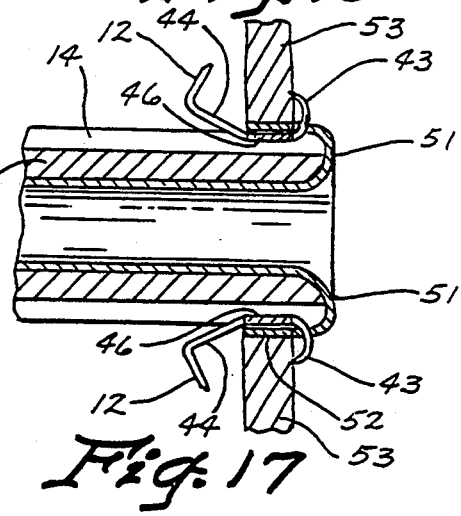
FIG. 17 comprises an enlarged side elevational detail view of the staple and blood vessel combination being disposed through a hole in a wall.

Following this, the stapling tool (10) may be manipulated to urge the forward end of the tool (10), the forward end of the staple (12), and the everted end of the blood vessel (51) through a hole (52) provided through the wall (53) of a second blood vessel or other appropriate structure as indicated in FIG. 17. The hole (52) provided through the wall (53) should be of an appropriate diameter to accommodate the exterior diameter of the blood vessel (51).

Figure 18:
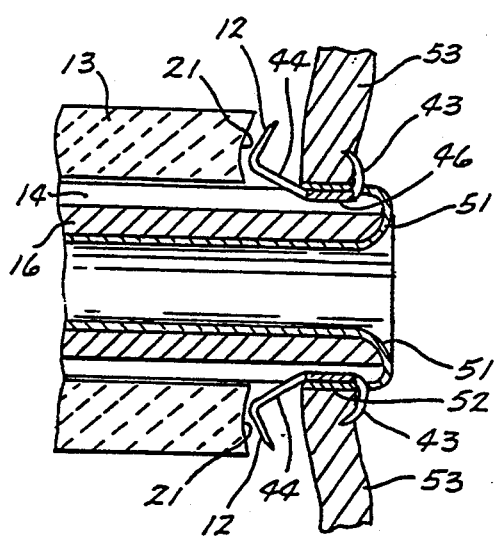
FIG. 18 comprises an enlarged side elevational detail view of the staple and blood vessel combination being retracted against the interior side of the wall.
Figure 19:
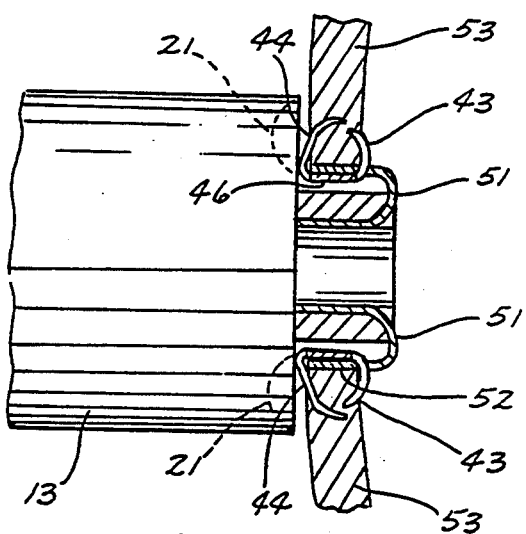
FIG. 19 is a view like FIG. 18, but showing the second set of exterior wall engaging members being pushed into their final position.

The stapling tool (10) may then be retracted somewhat to cause the plurality of vessel and interior wall engaging members (43) to pierce and become embedded in the interior side of the wall (53) as depicted in FIG. 18. Following this, the trigger unit (17) may be manipulated to cause the sleeve (13) to move forwardly and cause the anvil disposed on its forward end to contact the plurality of exterior wall engaging members (44) and thereby urge them forward into a piercing and engaging orientation as depicted in FIG. 19.

Following this, the mandrel (16) may be gently withdrawn from the stapling tool (10) to allow the fingers (26) of the core unit (14) to retract inwardly somewhat and thereby release their hold on the staple (12). The stapling tool (10) may then be gently withdrawn as a whole, leaving the blood vessel (51) firmly connected to the wall (53) in a stapled anastomosis.

Obviously, numerous modifications and variations of the present invention are possible in light of the above teachings. It is therefore to be understood that within the scope of the appended claims, the invention may be practiced otherwise than as specifically described therein.

We claim:

1. A method of connecting first and second blood vessels with a staple having a substantially rigid annular base member, a plurality of spaced apart first engaging members connected on a distal side of the annular base member and a plurality of spaced apart second engaging members connected on a proximal side of the annular base member, the method comprising:

providing a stapling instrument which includes:
a sleeve having a proximal end, a distal end, and an opening extending from the proximal end to the distal end;
a core unit slidably disposed within the opening in the sleeve, the core unit having a hole disposed longitudinally therethrough and wherein a distal portion of the core unit extends beyond the distal end of the sleeve;
a staple holder disposed on the distal portion of the core unit for selectively holding a staple thereon in a position in which first engaging members of the staple pointing generally distally;
a mandrel slidably disposed within the hole in the core unit, wherein the mandrel has a hollow center for receiving a first blood vessel and wherein the mandrel has a larger outside diameter than the inside diameter of the staple holder whereby the mandrel will force the staple holder outwardly to hold the staple when the mandrel is inside the staple holder; and
an actuator for moving the sleeve in a distal direction relative to the core unit;

placing the staple onto the staple holder;
inserting the mandrel into the hole in the core unit to a position at which the mandrel pushes the staple holder outwardly to securely hold the staple;
pulling a free end of a first blood vessel through the hollow center of the mandrel;
folding the free end of the first blood vessel over the first engaging members;
forcing the first engaging members through the first blood vessel;
deflectively bending the ends of the first engaging members radially outwardly and proximally;
forming an opening in a side of a second blood vessel;
inserting the first engaging members and the free end of the first blood vessel through the opening in the side of the second blood vessel while the staple and the first blood vessel are disposed on the staple holder and while keeping the second engaging members on the outside of the second blood vessel;
forcing the sleeve against the second engaging members by sliding the sleeve distally on the core unit using the actuator so that the second engaging members will pierce an outer wall of the second blood vessel around the opening in the side thereof and pull the first engaging members into piercing contact with an inner wall of the second blood vessel around the opening therein;
pulling the mandrel out of the hole in the core unit to an extent that the staple holder collapses inwardly to release its hold on the staple; and
pulling the stapling instrument, including the mandrel and core unit, off of the first blood vessel.

2. A stapling instrument for stapling a first vessel to a second vessel comprising:
a sleeve having a proximal end, a distal end, and a longitudinal bore therethrough, wherein the sleeve has a concave cavity formed annularly about the bore on the distal end of the sleeve for interaction with a staple;
a core unit slidably disposed within the bore of the sleeve wherein the core unit extends beyond the distal end of the sleeve, the core unit having a longitudinal bore therethrough and wherein the core unit is sized to hold a staple having first and second engaging members;
a mandrel slidably disposed for movement through the bore of the core unit, wherein the mandrel has a hollow center for receiving an end of a first vessel; and
an actuator for moving the sleeve into contact with the second engaging members of the staple to deflectively bend the second engaging members into piercing engagement with a side of a second vessel.

3. The instrument of claim 2 wherein the sleeve is a tubular member, having a circumferential channel formed adjacent the proximal end of the sleeve for interaction with the actuator.

4. The instrument of claim 2 wherein the sleeve is a plastic tube.

5. The instrument of claim 2 wherein the core unit includes a plurality of spaced apart fingers formed by slots in the core unit.

6. The instrument of claim 2 wherein the core unit is formed to hold the staple on the portion of the core that extends beyond the distal end of the sleeve.

7. The instrument of claim 2 wherein the core is a stainless steel tube.

8. The instrument of claim 2 wherein the mandrel is a stainless steel tube.

9. The instrument of claim 2 wherein the actuator comprises a handle portion, a trigger lever pivotally movable, about a pivot rod for engaging the sleeve to move the sleeve distally with respect to the core unit, and biasing means for biasing the trigger lever away from the sleeve.

10. A stapling instrument for stapling a first vessel to a second vessel comprising:
a sleeve having a proximal end, a distal end, and a longitudinal bore therethrough, wherein the sleeve has a concave cavity formed annularly about the bore on the distal end of the sleeve for interaction with a staple;
a core unit slidably disposed within the bore of the sleeve wherein the core unit extends beyond the distal end of the sleeve, the core unit having a longitudinal bore therethrough and wherein the core unit is sized to hold a staple having first and second engaging members, the staple is held by means of a plurality of spaced apart fingers formed by slots in the core unit;

a mandrel slidably disposed for movement through the bore of the core unit, wherein the mandrel has a hollow center for receiving an end of a first vessel, the mandrel being sized to force the fingers of the core unit outwardly to hold the staple when the mandrel is inside of the core unit; and an actuator for moving the sleeve into contact with the second engaging members of the staple to defectively bend the second engaging members into piercing engagement with a side of a second vessel.

11. The instrument of claim 10 wherein the sleeve is a tubular member, having a circumferential channel formed adjacent the proximal end of the sleeve for interaction with the actuator.

12. The instrument of claim 10 wherein the sleeve is a plastic tube.

13. The instrument of claim 10 wherein the core unit is formed to hold the staple on the portion of the core that extends beyond the distal end of the sleeve.

14. The instrument of claim 10 wherein the core is a stainless steel tube.

15. The instrument of claim 10 wherein the mandrel is a stainless steel tube.

16. The instrument of claim 10 wherein the actuator comprises a handle portion, a trigger lever pivotally movable about a pivot rod for engaging the sleeve to move the sleeve distally with respect to the core unit, and biasing means for biasing the trigger lever away from the sleeve.

* * * * *